United States Patent [19]

Karashima

[11] Patent Number: 4,806,072

[45] Date of Patent: Feb. 21, 1989

[54] METHOD AND APPARATUS FOR KEEPING AND SUPPLEMENTING GOODS

[75] Inventor: Etsuo Karashima, Ebina, Japan

[73] Assignee: Nisshin Kogyo Kabushiki Kaisha, Tokyo, Japan

[21] Appl. No.: 97,644

[22] Filed: Sep. 16, 1987

[30] Foreign Application Priority Data

Aug. 4, 1987 [JP] Japan .................. 62-193659

[51] Int. Cl.$^4$ .............................................. B65G 3/00
[52] U.S. Cl. ..................................... 414/786; 414/331; 414/267
[58] Field of Search ................ 211/133, 126; 414/331, 414/786, 266, 267, 277; 186/62, 7, 52

[56] References Cited

U.S. PATENT DOCUMENTS

| | | | |
|---|---|---|---|
| 2,741,371 | 4/1956 | Oswalt | 414/266 X |
| 3,687,312 | 8/1972 | Weir | 414/267 |
| 4,466,765 | 8/1984 | Mautino | 414/277 |

Primary Examiner—Reinaldo P. Machado
Assistant Examiner—Sarah A. Lechok Eley
Attorney, Agent, or Firm—Wenderoth, Lind & Ponack

[57] ABSTRACT

A method for keeping goods and, if necessary, supplementing them to showcases in a shopping floor is disclosed. Also an apparatus to be used for practicing this method is disclosed. A group of temporary goods keeping carts each having multi-level shelves are disposed on standby at a temporary goods holding place in a store warehouse leading to a shopping floor, good receiving carts brought into the warehouse and the temporary goods keeping carts are moved to working tables within the warehouse, where the goods on the goods receiving carts are classified and accommodated in goods holding trays, thereafter the trays are placed on the respective shelves in the temporary goods keeping carts, then the temporary goods keeping carts are returned to the temporary goods holding place, subsequently goods supplementing carts each having shelves at a plurality of levels are brought to the temporary goods holding place, the trays on the respective shelves in the temporary goods keeping carts are transferred onto the respective shelves in the goods supplementing carts, then the goods supplementing carts are brought to the shopping floor, or the temporary goods keeping carts are directly brought to the shopping floor, and the goods in the trays on the respective shelves in the goods supplementing carts or in the temporary goods keeping carts are displayed in showcases in the shopping floor.

2 Claims, 12 Drawing Sheets

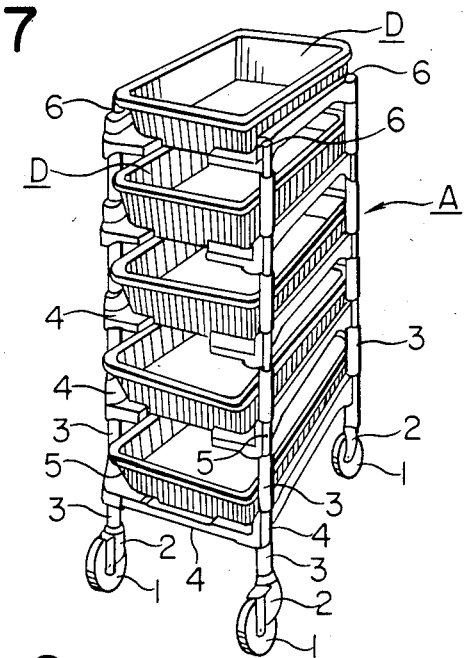
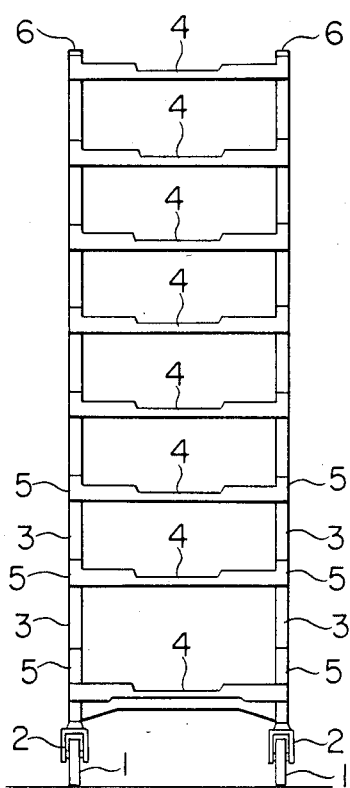
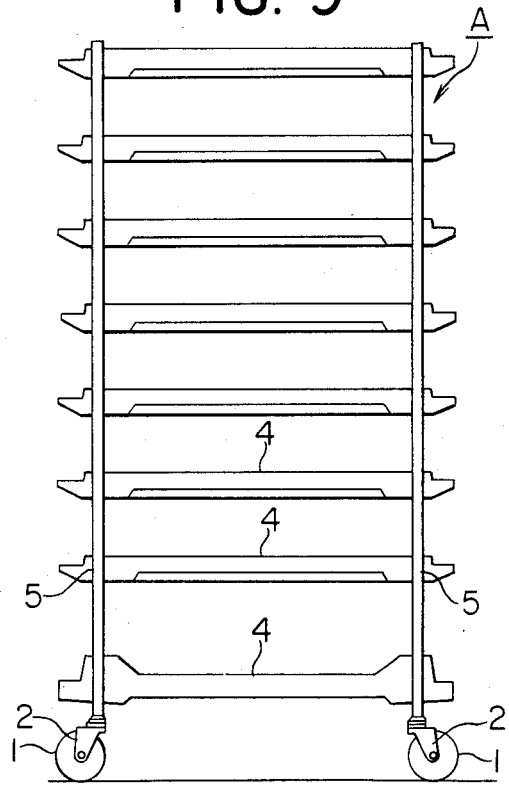

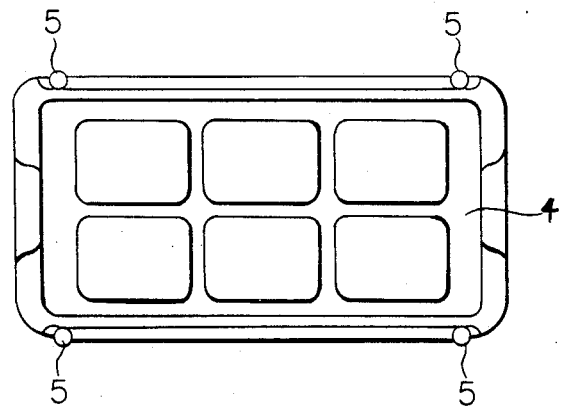
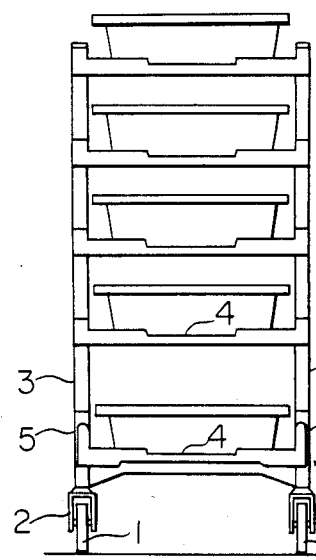
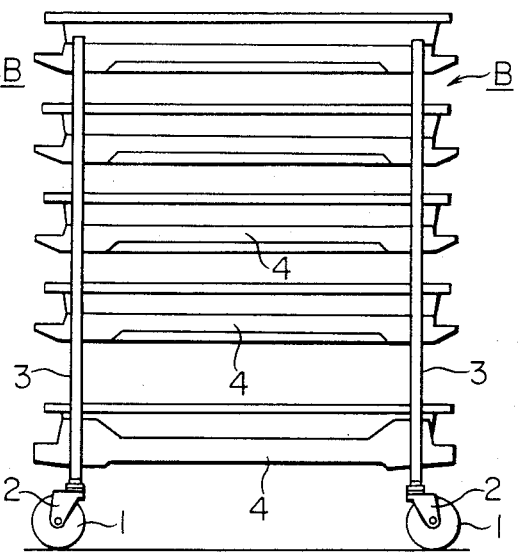
FIG. 10
FIG. 11
FIG. 12

METHOD AND APPARATUS FOR KEEPING AND SUPPLEMENTING GOODS

BACKGROUND OF THE INVENTION

1. Field of the Invention

The present invention relates to a method for keeping and supplementing goods in a supermarket, a department store, or the like, and an apparatus for practicing the method.

2. Description of the Prior Art

Heretofore, goods delivered to a goods receiving station as packed in corrugated cardboard boxes or the like were reloaded on a cart and carried to a store warehouse, then they were unpacked in a shop and supplementarily displayed in a showcase, while goods left without being supplemented were held packed in the above-mentioned corrugated cardboard boxes, and these boxes were kept under the condition of being stacked on a floor of the warehouse, on a palette or on the cart.

Accordingly, in the prior art method as described above, it was impossible to know the amount of goods contained in corrugated cardboard boxes stacked under other boxes, and in order to take out goods contained in a box stacked under other boxes, excessively large labor would be forced upon a person.

Moreover, an empty space within a corrugated cardboard box was a wasteful space, and it would increase the space of the warehouse in vain.

SUMMARY OF THE INVENTION

It is therefore one object of the present invention to provide a novel method for keeping and supplementing goods, which enables a worker to easily check the amount of goods being kept in a store warehouse, which does not necessitate excessive labor for taking out goods contained in a box stacked under other boxes as is the case with the prior art method, and which can save wasteful space in a store warehouse.

Another object of the present invention is to provide an apparatus for keeping and supplementing goods, which is suitable to be used for practicing the above-mentioned method.

According to one feature of the present invention, there is provided a method for keeping and supplementing goods consisting of the steps of disposing a group of temporary goods keeping carts each having shelves at a plurality of levels on standby at a temporary goods holding place in a store warehouse leading to a shopping floor, moving goods receiving carts brought into the warehouse and the temporary goods keeping carts to working tables within the warehouse, classifying the goods on the goods receiving carts and accommodating them in goods holding trays on the working tables, thereafter placing the trays on the respective shelves in the temporary goods keeping carts, then returning the temporary goods keeping carts to the temporary goods holding place, subsequently bringing goods supplementing carts each having shelves at a plurality of levels to the temporary goods holding place, transferring the trays on the respective shelves in the temporary goods keeping carts onto the respective shelves in the goods supplementing carts, then bringing the goods supplementing carts to the shopping floor, or directly bringing the temporary goods keeping carts to the shopping floor, and displaying the goods in the trays on the respective shelves in the goods supplementing carts or in the temporary goods keeping carts in showcases in the shopping floor.

According to another feature of the present invention, there is provided an apparatus for keeping and supplementing goods comprising temporary goods keeping carts having shelves at a plurality of levels mounted to posts erected on a traveling truck and adapted to travel back and forth between working tables for classifying goods in a store warehouse and a temporary goods holding place leading to a shopping floor, goods supplementing carts having shelves at a plurality of levels mounted to posts erected on a traveling truck and adapted to travel back and forth between the temporary goods holding place and the shopping floor, goods accommodating multi-level shelves disposed within the warehouse, and goods holding trays adapted to be placed on the goods accommodating multi-level shelves as well as the shelves in the respective carts.

Upon practicing the above-featured invention, the goods receiving carts loaded with corrugated cardboard boxes accommodating goods and brought into the store warehouse are moved to the working tables in the warehouse, also goods accommodating trays are placed in an overlapped relationship on temporary goods keeping carts having shelves at a plurality of levels, which carts are disposed on standby at the temporary goods holding place within the warehouse leading to the shopping floor, then the temporary goods keeping carts are moved to the above-mentioned working tables, on which the corrugated cardboard boxes on the goods receiving carts are unpacked and the goods in the boxes are classified and accommodated in the above-described respective trays, the respective trays are placed on the shelves at the respective levels in the temporary goods keeping carts, and thereafter the carts are returned to the above-mentioned temporary goods holding place. Subsequently, the goods supplementing carts having shelves at a plurality of levels are brought into the temporary goods holding place, and the trays on the respective shelves in the temporary goods keeping carts are transferred onto the respective shelves in the goods supplementing carts.

The goods supplementing carts having the trays accommodating the thus classified goods placed on the respective shelves, are brought into the shopping floor, and then the goods in the above-described trays are supplemented to an displayed on the respective shelves in showcases in the shopping floor.

In some cases, the above-described temporary goods keeping carts are directly brought into the shopping floor.

According to the present invention, as described above, since the goods received and classified in the store warehouse are accommodated in goods holding trays and these trays are placed and kept on shelves in multi-level type carts disposed within the warehouse, goods in stock would not be stacked under other goods as packed in a box as is the case with the prior art method, the location and amount of goods can be confirmed at a glance, and upon taking out goods, it becomes unnecessary to open a corrugated cardboard box each time as is the case with the prior art method.

Thus, according to the present invention, the work of seeking for desired goods in a warehouse is saved, the labor for taking out goods stacked under other goods becomes unnecessary, hence undesirable stocks are eliminated, and a revolving rate of goods is improved.

Furthermore, according to the present invention, owing to the fact that supplement and display of goods are effected by making use of a group of temporary goods keeping carts and goods supplementing carts each having shelves at a plurality of levels and goods holding trays which can be transferred between the shelves in the respective carts, a working efficiency can be greatly improved.

The above-mentioned and other objects, features and advantages of the present invention will become more apparent by reference to the following description of preferred embodiment of the invention taken in conjunction with the accompanying drawings.

BRIEF DESCRIPTION OF THE DRAWINGS

In the accompanying drawings:

FIG. 7 is a perspective view of a temporary goods keeping cart;

FIG. 8 is a front view of the same cart;

FIG. 9 is a side view of the same cart;

FIG. 10 is a plan view of the same cart;

FIG. 11 is a front view of a goods supplementing cart;

FIG. 12 is a side view of the same cart;

DESCRIPTION OF THE PREFERRED EMBODIMENT

Figure 1:
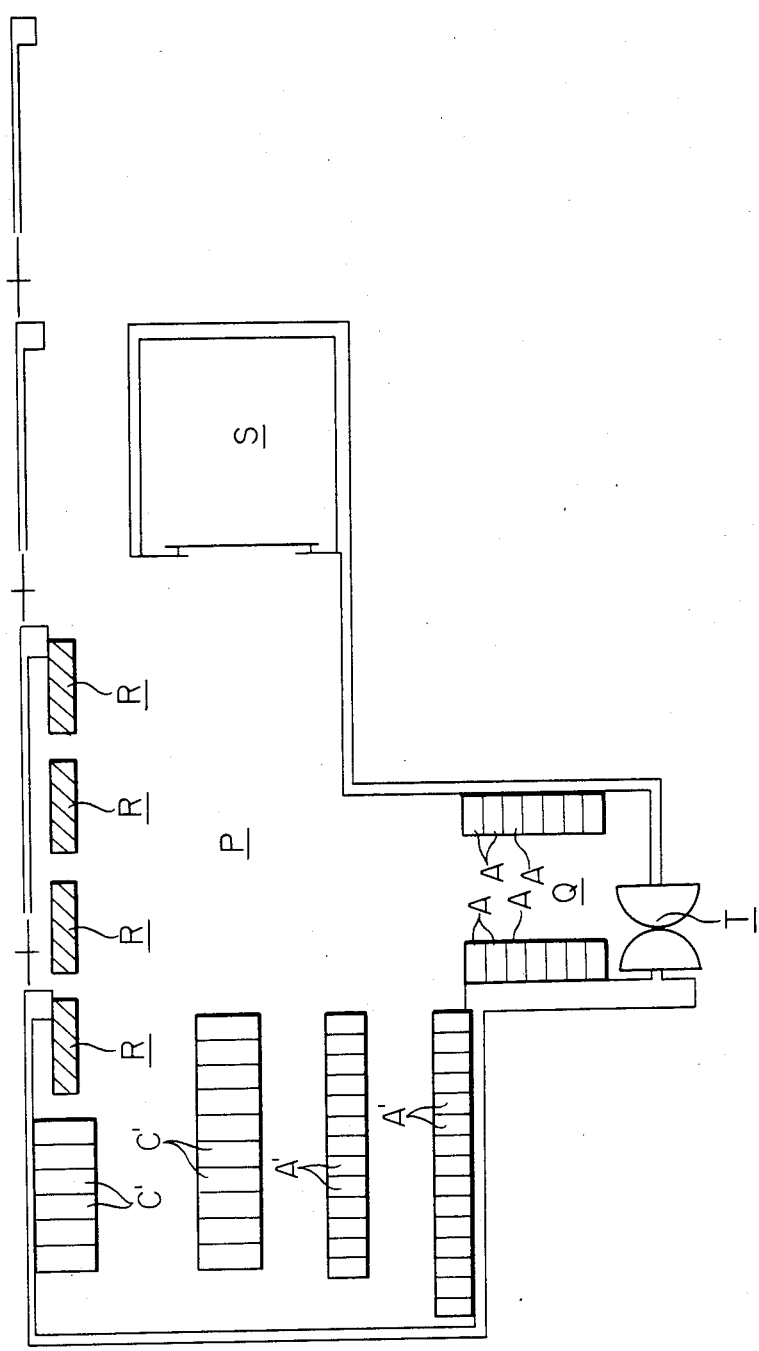
FIGS. 1 to 6 are plan views showing successive steps in one preferred embodiment of the method according to the present invention.

In the following, the present invention will be described in connection to the illustrated embodiment.

Reference character (A) designates a temporary goods keeping cart, in which spacer tubes (3) and sleeves (5) provided at four corners of shelf plates (4) are alternately fitted around respective tubular posts at four corners erected from caster frames (2) at four corners having rollers (1) at their bottom, and elastic caps (6) are fitted to the top of the above-mentioned posts (See FIGS. 7 to 10). It is to be noted that details of the above-described cart (A) are disclosed in Japanese Utility Model Publication No. 54-17945 (1979).

Reference character (B) designates a goods supplementing cart, which has the same structure as the above-described temporary goods keeping cart (A), but is constructed lower in height than the latter as shown in FIGS. 11 and 12.

Figure 13:
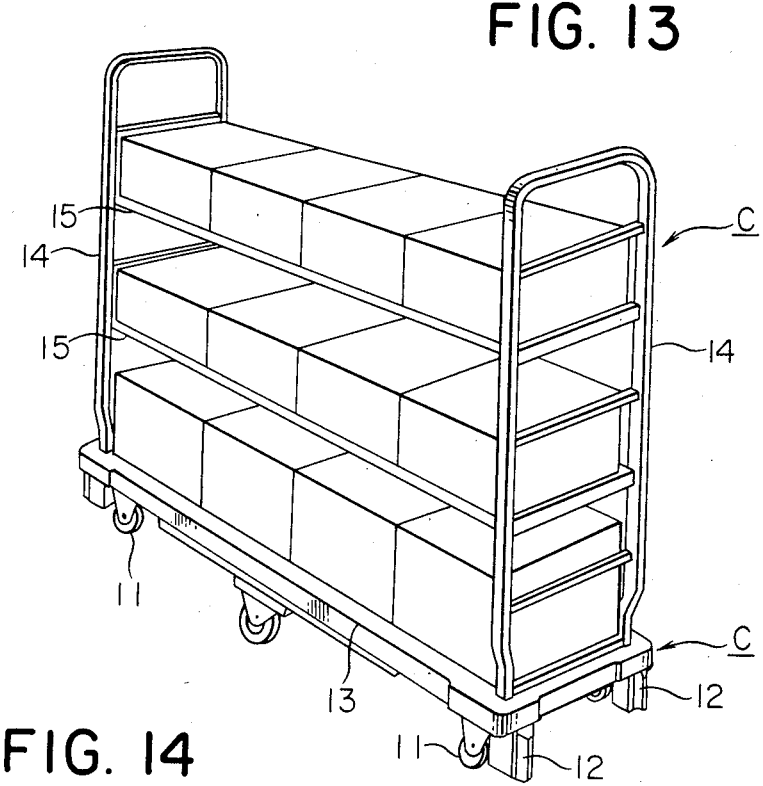
FIG. 13 is a perspective view of a goods receiving cart.

Reference character (C) designates a goods receiving cart, in which casters (11) are provided on the bottom surface, and shelf plates (15) are bridged at a desired number of levels between post members (14) erected on the opposite sides of a rectangular base frame (13) provided with bumper rubbers (12) at its four corners as shown in FIG. 13. It is to be noted that details of this cart is disclosed in Japanese Laid-Open Utility Model Specification No. 56-9965 (1981).

As shown in FIG. 1, the above-described temporary goods holding carts (A) are arrayed on standby at a temporary goods holding place (Q) in a store warehouse (P) leading to a shopping floor.

In this figure, reference character (R) designates working tables disposed on the opposite side to the above-mentioned temporary goods holding place (Q), reference character (S) designates an elevator hole, and reference character (T) designates a doorway leading to a shopping floor.

In addition, in the above-described warehouse (P) are disposed stock keeping carts (A') having the same construction as the above-described temporary goods keeping cart (A), and large-sized stock keeping carts (C') of multi-level type having the same construction as the above-described goods receiving cart (C) and to be used for keeping large-sized or heavy goods which cannot be kept by means of the stock keeping cart (A').

It is to be noted that both or either one of the stock keeping carts (A') and (C') could be modified to multi-level type fixed shelves not provided with casters.

Figure 2:
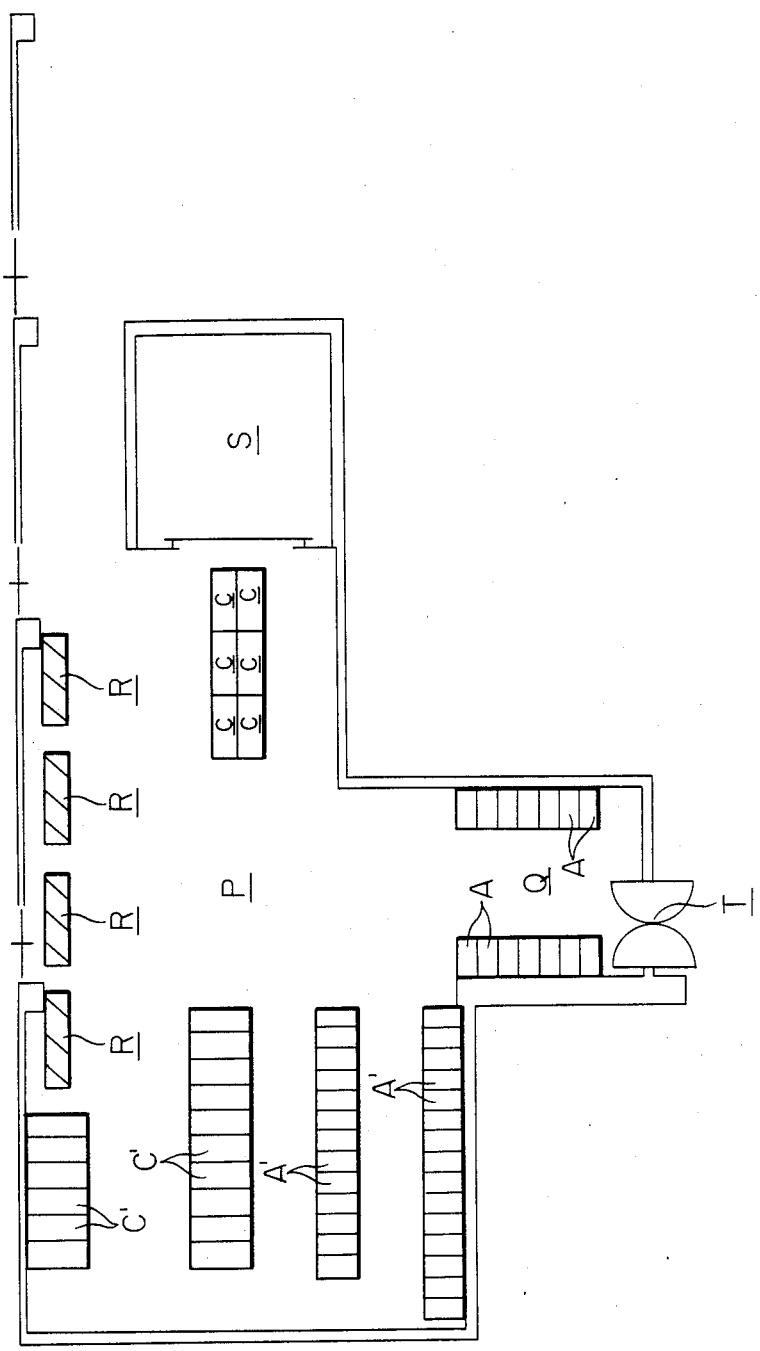

At first, the goods receiving carts (C) loaded with goods packed in corrugated cardboard boxes which were received at a goods receiving station (not shown) are brought into the store warehouse (P) by means of an elevator (See FIG. 2).

Figure 3:
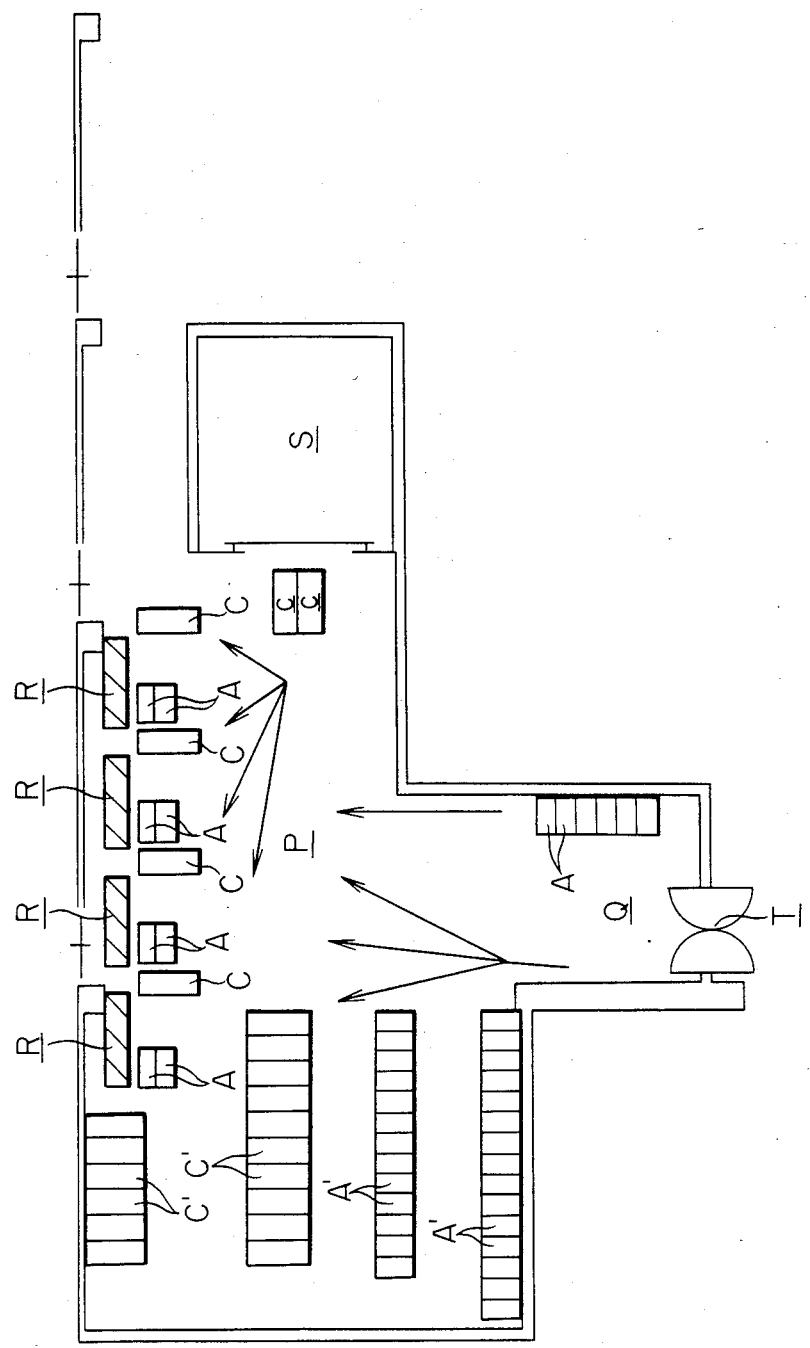
Figure 4:
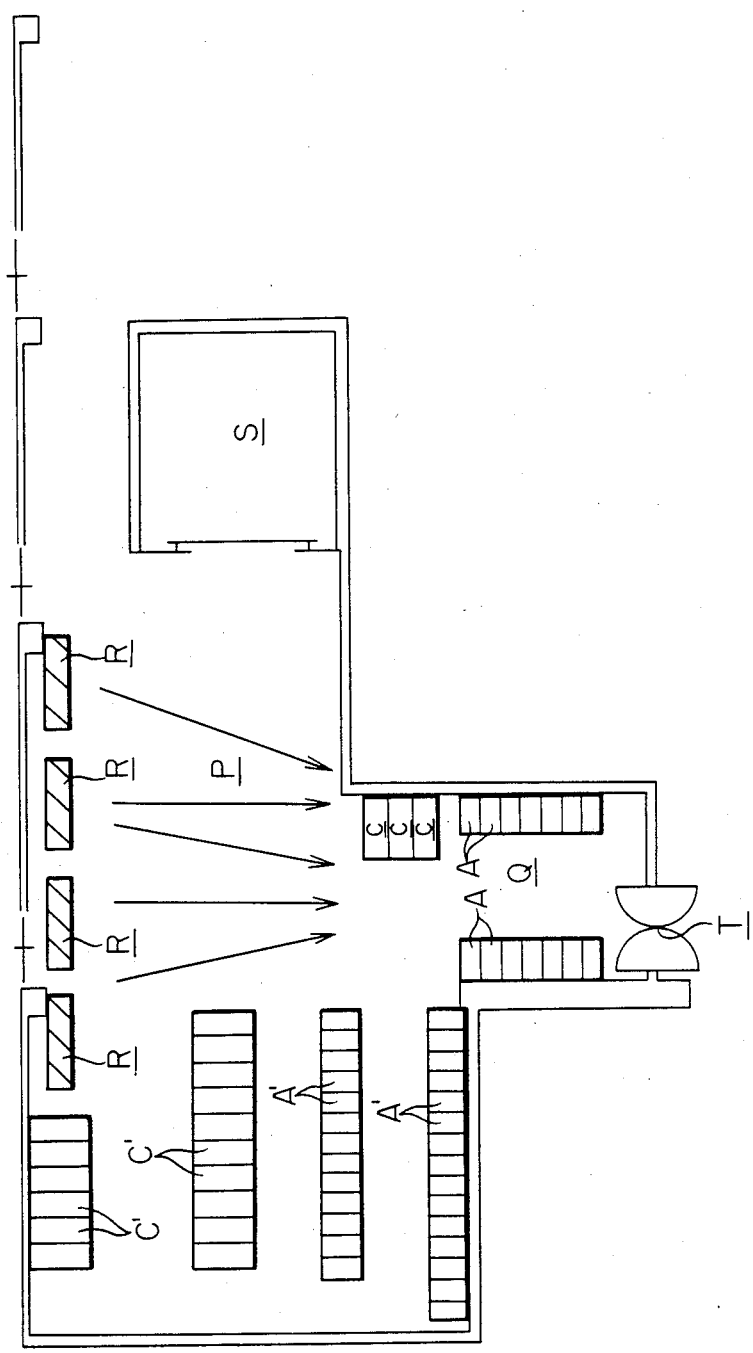

Thereafter, the goods receiving carts (C) are moved to the working tables (R), and also the temporary goods keeping carts (A) having goods holding trays (D) of vat-shape mounted on the shelf plates (4) in an overlapped relationship are moved to the working table (R) to be opposed to the goods receiving carts (C) (See FIG. 3).

Figure 15:
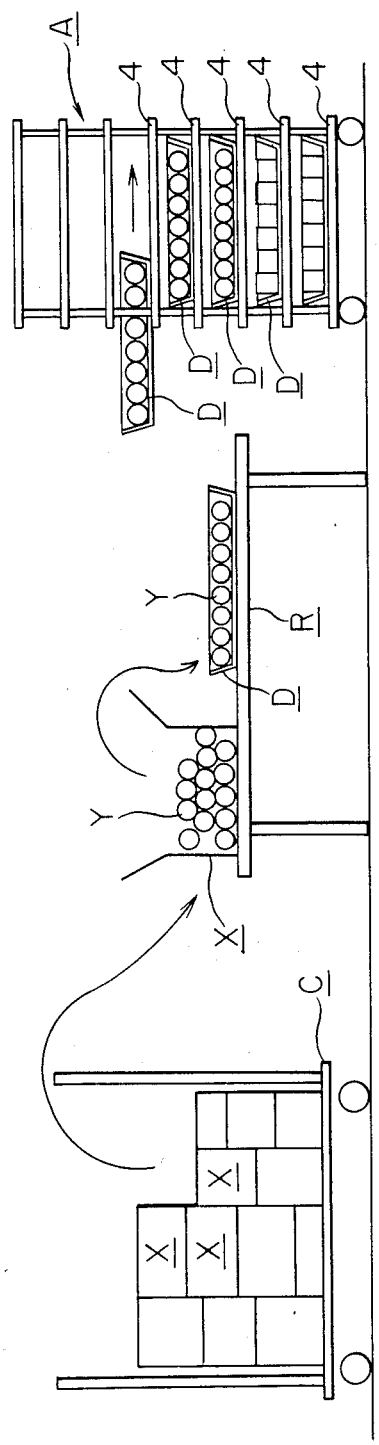
FIG. 15 is a schematic vertical cross-section view showing the state of checking and classifying operations.

Then, goods (Y) packed in a corrugated cardboard box (X) transferred from the goods receiving cart (C) onto the working table (R) are classified and accommodated in the goods holding trays (D) transferred from the temporary goods keeping cart (A) onto the working table (R), and the goods holding trays (D) accommodating the goods (Y) are placed on the respective shelf plates (4) in the temporary goods keeping cart (A) (See FIG. 15).

After the classification of goods has been finished, the temporary goods keeping cart (A) having the above-mentioned trays (D) accommodating the goods (Y) placed thereon is returned to the temporary goods holding place (Q).

At this time, large-sized goods or heavy articles which cannot be accommodated in the temporary goods keeping cart (A) are held loaded on the goods receiving cart (C), and the cart (C) is itself moved to a side of the temporary goods keeping carts (A) at the temporary goods holding place (Q).

Figure 5:
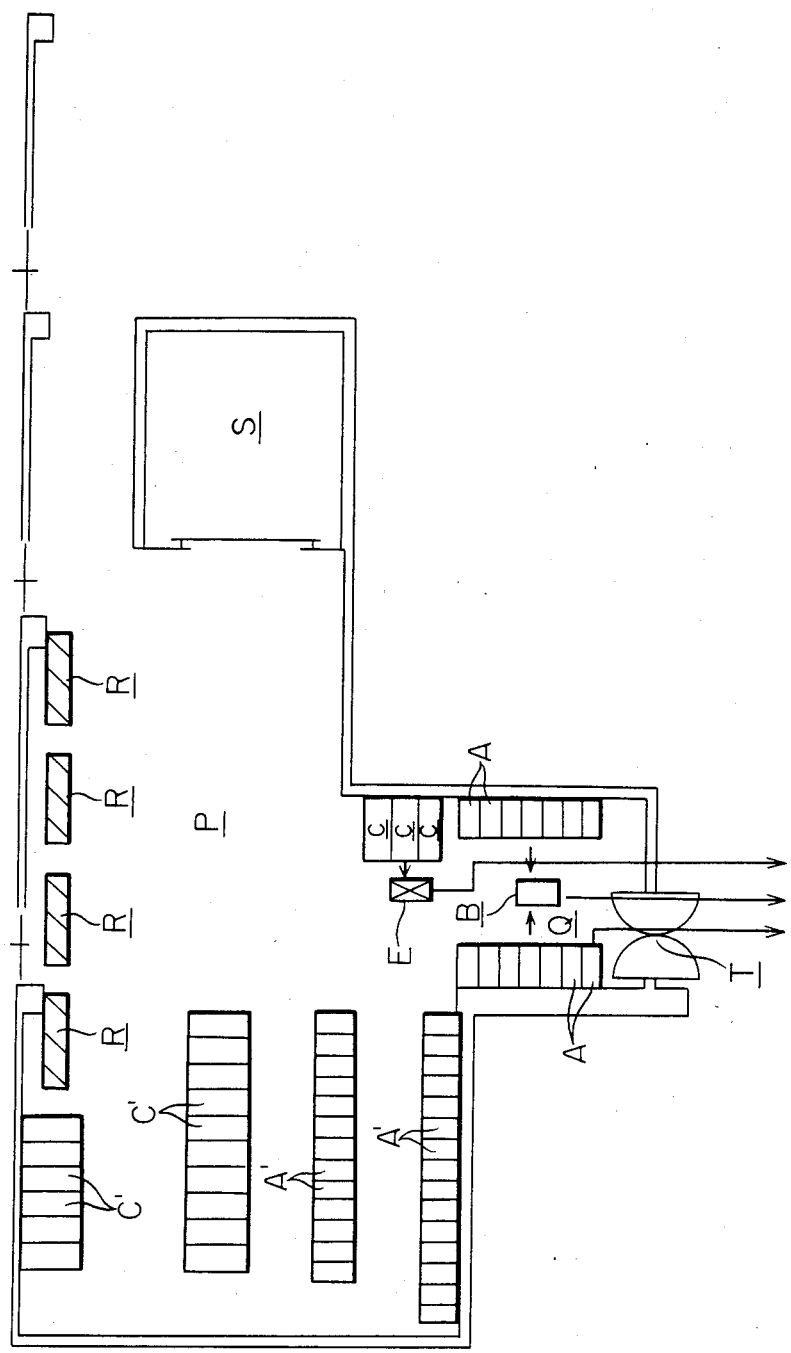
Figure 16:
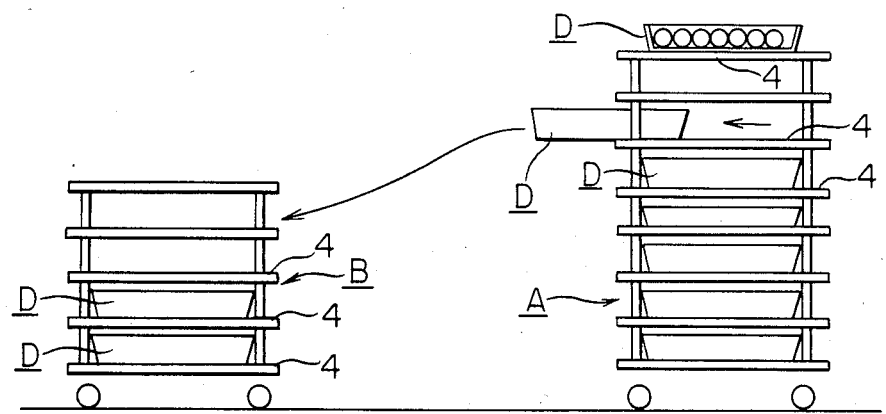
FIG. 16 is a schematic vertical cross-section view showing the state of a pre-operation for supplementing goods to a shopping floor in a store.

Subsequently, a goods supplementing cart (B) is brought into the temporary goods holding place (Q), the trays (D) accommodating the goods (Y) and placed on the shelf plates (4) in the temporary goods keeping cart (A) are taken out and transferred onto the shelf plates (4) in the aforementioned goods supplementing cart (B) (See FIG. 16), and this cart (B) is carried to the shopping floor. It is to be noted that goods kept at the temporary goods holding place (Q) while being held loaded on the goods receiving cart (C) because of being unable to be accommodated in the temporary goods keeping cart (A), are transferred to a large-sized goods supplementing cart (E), and the cart (E) is carried to the shopping floor (See FIG. 5).

Figure 14:
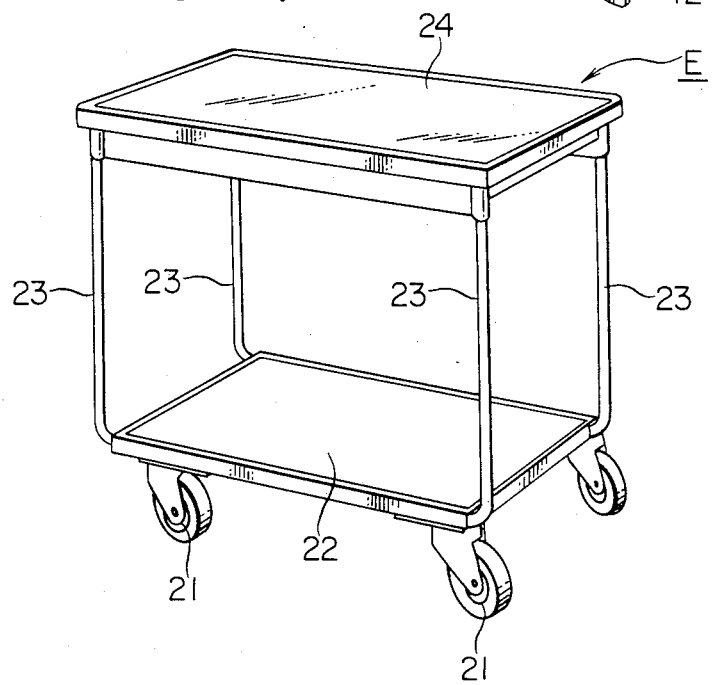
FIG. 14 is a perspective view of a cart for large goods or heavy articles.

It is also to be noted that in order to facilitate transfer of large-sized or heavy goods, the large-sized goods supplementing cart (E) has the construction shown in FIG. 14, in which an upper panel (24) is supported at the top of posts (23) erected at four corners of a lower panel (22) provided with casters (21).

Figure 6:
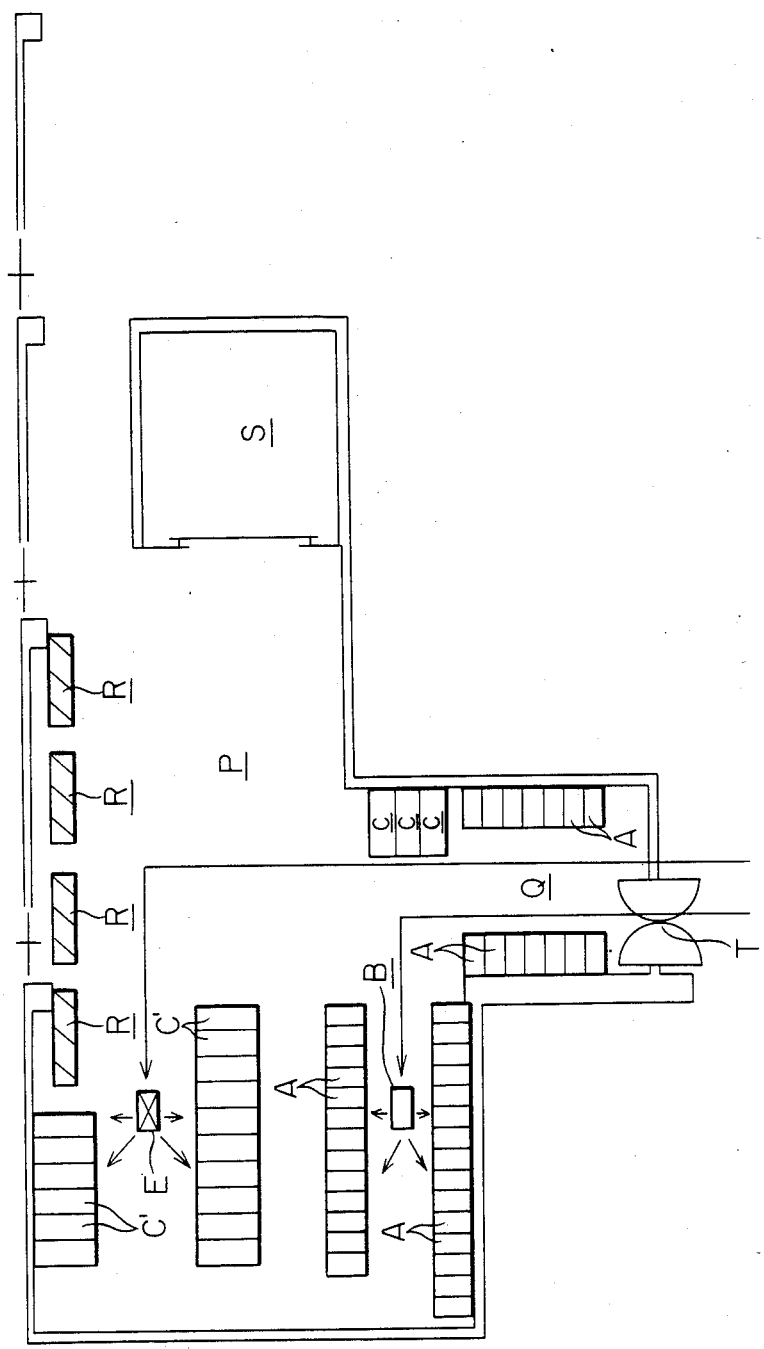
Figure 17:
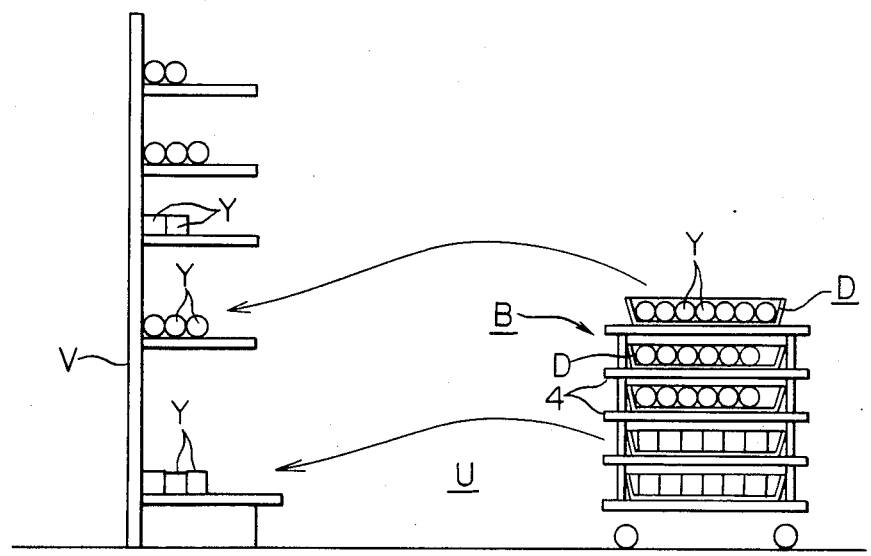
FIG. 17 is a schematic vertical cross-section view showing the state of operations for supplementing and displaying goods.
Figure 18:
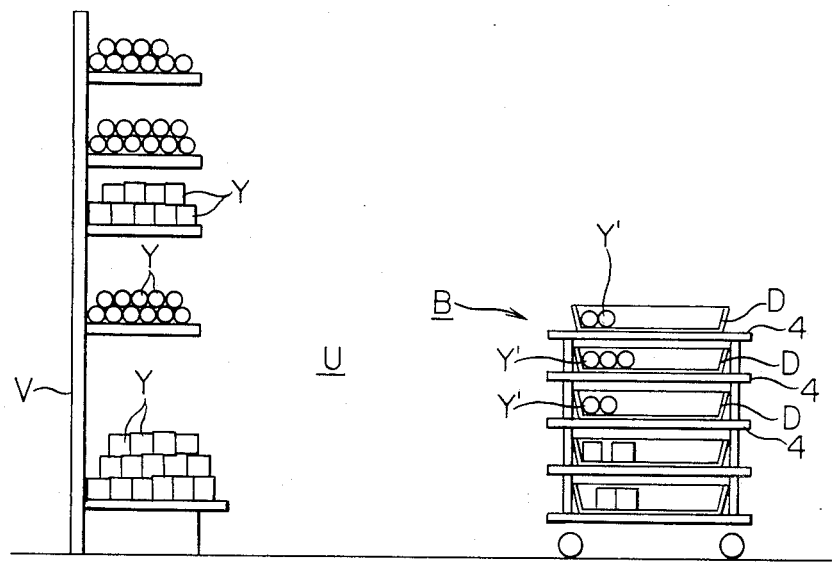
FIG. 18 is a schematic vertical cross-section view showing the state upon completion of the goods supplementing and displaying operations.
Figure 19:
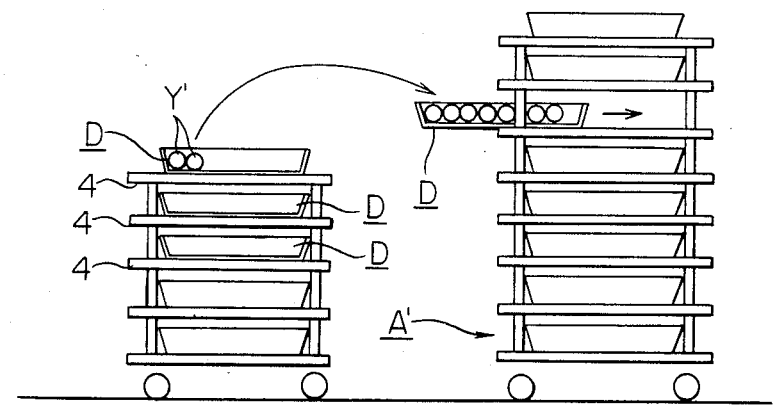
FIG. 19 is a schematic vertical cross-section view showing the state of a processing operation for good left without being supplemented.

Then, in the shopping floor (U), the goods (Y) accommodated in the trays (D) on the respective shelf plates (4) in the goods supplementing cart (B) carried to the shopping floor (U) in the store, are supplementarily displayed on the respective shelf plates in a showcase (V) (See FIG. 17), after the supplementary display work has completed, goods (Y') left unsupplemented are accommodated in the trays (D) on the shelf plates (4) in the above-described supplementing cart (B) (See FIG. 18), this cart (B) is returned into the store warehouse (P) as shown in FIG. 6 the trays in which goods left unsupplemented are classified and accommodated, are placed on the shelf plates in the stock keeping carts (A'), and thereby these goods left unsupplemented are kept (See FIG. 19).

When the large-sized goods supplementing cart (E) is used, also after the goods on the cart (E) have been supplementarily displayed on the respective shelf plates in the showcase (V) in the shopping floor (U), the cart (E) is returned to the store warehouse (P) as shown in FIG. 6, and then the remaining goods are returned onto the shelf plates in the above-described large-sized stock keeping cart (C') and kept there.

Alternatively, the temporary goods keeping cart (A) could be directly brought into the shopping floor.

While the present invention has been described above in connection to one preferred embodiment thereof, as a matter of course, it is intended that all matter contained in the above-description and illustrated in the accompanying drawings shall be interpreted to be illustrative and not as a limitation to the scope of the invention.

What is claimed is:

1. A method for keeping and supplementing goods, characterized by the steps of disposing a group of temporary goods keeping carts each having shelves at a plurality of levels, on standby, at a temporary goods holding place in a store warehouse leading to a shopping floor, moving goods receiving carts brought into said warehouse and said temporary goods keeping carts to working tables within the warehouse, classifying the goods on said goods receiving carts and accommodating them in goods holding trays on said working tables, thereafter placing said trays on the respective shelves in said temporary goods keeping carts, then returning said temporary goods keeping carts to said temporary goods holding place, subsequently bringing goods supplementing carts each having shelves at a plurality of levels to said temporary goods holding place, transferring the trays on the respective shelves in said temporary goods keeping carts onto the respective shelves in said goods supplementing carts, then bringing said goods supplementing carts to the shopping floor, or directly bringing said temporary goods keeping carts to the shopping floor, and displaying the goods in the trays on the respective shelves in said goods supplementing carts or in said temporary goods keeping carts in showcases in the shopping floor.

2. A method for keeping and supplementing goods as claimed in claim 1, further characterized by the additional steps of moving said goods supplementing carts having trays accommodating goods left without being supplemented to the showcases placed on their shelves to the store warehouse, and transferring said trays onto multi-level shelves in said warehouse.

* * * * *